United States Patent [19]

Stoutamire et al.

[11] Patent Number: 4,681,947

[45] Date of Patent: Jul. 21, 1987

[54] PREPARATION OF OPTICALLY-ACTIVE CYANOMETHYL ESTERS

[76] Inventors: Donald W. Stoutamire, 904 Bel Passi Dr.; Charles H. Tieman, 2209 Fremont St., both of Modesto, Calif. 95350

[21] Appl. No.: 692,472

[22] Filed: Jan. 18, 1985

Related U.S. Application Data

[60] Division of Ser. No. 551,652, Nov. 14, 1983, Pat. No. 4,560,515, which is a continuation-in-part of Ser. No. 443,513, Nov. 22, 1982, abandoned.

[51] Int. Cl.$^4$ ............................................. B01J 31/00
[52] U.S. Cl. ..................................... 544/370; 502/167
[58] Field of Search ................ 260/112.5 R; 548/294; 502/167

[56] References Cited

U.S. PATENT DOCUMENTS 4,086,219  4/1978  Wittle et al. .............. 260/112.5 LH

OTHER PUBLICATIONS

Chem. Abstr., vol. 102, (1985) 5947y and 112889c.
Oku et al., *Makromol. Chem.*, 183, 579-586, (1982).
Oku et al., *J.C.S. Chem. Comm.*, No. 5, 229-230, (1981).

*Primary Examiner*—Delbert R. Phillips
*Attorney, Agent, or Firm*—Nancy Joyce Gracey

[57] ABSTRACT

Optically-active alpha-cyano esters are prepared by treating a non-symmetrical ketene with a racemic or an optically-active alpha-hydroxynitrile or with an aldehyde and cyanide ions in the presence of an optically-active amine catalyst.

2 Claims, No Drawings

PREPARATION OF OPTICALLY-ACTIVE CYANOMETHYL ESTERS

CROSS REFERENCE TO RELATED APPLICATIONS

This is a division of application Ser. No. 551,652, filed Nov. 14, 1983, now U.S. Pat. No. 4,560,515, which is a continuation-in-part of Ser. No. 443,513 filed Nov. 22, 1982, now abandoned.

BACKGROUND OF THE INVENTION

1. Field of the Invention

The present invention is directed to processes for the preparation of optically-active cyanomethyl esters and novel catalysts therefor.

2. Description of the Prior Art

Stereoisomers of cyanomethyl esters of alpha-chiral carboxylic acids or the acids themselves usually have different effects in biological systems. In the past, it usually had not been simple to prepare such optically-active cyanomethyl esters directly because the corresponding chiral alpha-hydroxynitriles were not always readily available. Even when these optically-active alpha-hydroxynitriles were available or became more readily available, the optically-active acids were not always readily accessible. Often, the optically-active acids were obtained by classical resolution, which was usually time consuming and not practical on a large scale.

The present process provides a process for preparing optically-active cyanomethyl esters of alpha-chiral carboxylic acids in high yield by a direct synthesis method, avoiding the cumbersome classical resolution of the corresponding optically-active acids and alcohols.

SUMMARY OF THE INVENTION

The present invention is directed to a process for the preparation of an optically-active cyanomethyl ester of an alpha-chiral (optically-active) carboxylic acid (i.e. alpha-chiral cyanomethyl esters of alpha-chiral carboxylic acids), or a mixture enriched therein, which comprises treating a non-symmetrical ketene with a racemic or an optically-active alpha-hydroxynitrile in the presence of an optically-active (chiral) tertiary amine catalyst. The optically-active cyanomethyl ester products include those of formula I below

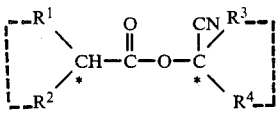

wherein $R^1$, $R^2$, $R^3$ and $R^4$ are substituents; *denotes the asymmetrically substituted carbon atom, and the broken lines are optional bonds.

The reaction is conducted in the presence or absence of a solvent. When a solvent is used the solvent is preferably a non-hydroxylic solvent such as hydrocarbons, chlorinated hydrocarbons, ethers and the like. For example, suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between 40° and 65° C., between 60° and 80° C. or between 80° and 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Suitable chlorinated hydrocarbons contain from 1 to 4 chlorine atoms in combination with an alkane chain containing from 1 to 4 carbon atoms or with a benzene ring, for example, carbon tetrachloride, chloroform, dichloromethane, 1,2-dichloroethane, trichloroethane, perchloroethane, chlorobenzene and 1,2- or 1,3-dichlorobenzene and the like. Ethers are generally those containing from 4 to 6 carbon atoms such as diethyl ether, methyl tert-butyl ether and diisopropyl ether and the like. The solvent is preferably an aromatic solvent, especially toluene.

Any non-symmetrical ketene is useful (provided it does not contain substituent groups which form other stable reaction products with the alpha-hydroxynitrile. The non-symmetrical ketenes have the formula II

wherein $R^1$ and $R^2$ each independently is a different alkyl, aralkyl, alkoxy, aryloxy, alkylthio, alkylsulfonyl, arylthio, or arylsulfonyl group containing from 1 to 10 carbon atoms, or a cycloalkyl group containing 3 to 7 ring carbon atoms, or $R^2$ is also an alkenyl or alkynyl group containing 2 to 10 carbon atoms; a naphthyl group; a phenyl group; a heterocyclic group containing 5 or 6 ring atoms, one of which is oxygen, sulfur or nitrogen, and the remainder are carbon atoms; or an amino group disubstituted by actyl or alkyl containing up to 10 carbon atoms or a phenyl group; or $R^1$ and $R^2$, when taken together with the carbon atom to which they are attached, form a non-symmetrical cycloalkyl group containing 4 to 7 ring carbon atoms and 4 to 14 carbon atoms. The $R^1$ and $R^2$ groups can be optionally substituted by one or more of halogen atoms having an atomic number of from 9 to 35, alkyl or haloalkyl containing 1 to 4 carbon atoms, alkenyl or haloalkenyl containing 2 to 4 carbon atoms, haloalkoxy or alkoxy of 1 to 4 carbon atoms, haloalkylthio or alkylthio of 1 to 4 carbon atoms or equivalent kinds and sizes of substituents which may contain the same or greater carbon number.

One embodiment of non-symmetrical ketenes used in the process of the invention is that which results in the pyrethroid esters, including those esters having an acid moiety described in U.S. Pat. Nos. 4,062,968 and 4,199,595. Examples of such ketenes include those having the formula II in which $R^1$ is isopropyl or cyclopropyl optionally substituted by one or more chlorine atoms; $R^2$ is an alkyl group containing 1 to 6 carbon atoms; an alkenyl group containing 2 to 6 carbon atoms; a naphthyl group; a phenyl group or a (benzyloxycarbonyl)phenylamino group, each optionally ring-substituted by one or more of halogen, alkyl, haloalkyl, alkoxy or haloalkoxy in which the halogens are bromine, chlorine or fluorine, and the alkyl groups contain 1 to 4 carbon atoms.

Of particular interest as non-symmetrical ketene reactants because their resulting esters are usually highly pesticidally active are those ketenes having the formula II in which $R^1$ is isopropyl; $R^2$ is a phenyl group para-substituted by halogen, alkyl, haloalkoxy in which the halogen is, e.g. chlorine or fluorine, and the alkyl contains 1 to 4 carbon atoms, e.g. methyl.

For example, the non-symmetrical ketene is (4-chlorophenyl)isopropylketene, (4-(difluoromethoxy)-phenyl)isopropylketene, ((4-trifluoromethyl)-3-chlorophenyl)(benzyloxycarbonyl)amino)isopropylketene, and the like.

Any racemic or optically-active alpha-hydroxynitrile is useful (provided it does not contain substituent groups which form outer stable reaction products with the non-symmetrical ketene or the catalyst). Preferably, the alpha-hydroxynitrile is a symmetrical or non-symmetrical, racemic or optically-active alpha-hydroxynitrile of formula III

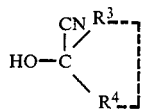

wherein $R^3$ is an optionally-substituted hydrocarbyl or heterocyclic group; and $R^4$ is an optionally substituted hydrocarbonyl group or a hydrogen atom or $R^3$ and $R^4$ together with the carbon atom to which they are attached form a carbocyclic group as denoted by the dotted line.

The hydrocarbyl groups represented by $R^3$ and $R^4$ in the formula III may be, for example, an alkyl, a cycloalkyl or an aryl group of up to 20 carbon atoms, preferably up to 10 carbon atoms, or $R^3$ in the formula III may be a carbocyclic or an O or S heterocyclic aryl group. Examples of carbocyclic aryl groups are phenyl, 1-naphthyl, 2-naphthyl and 2-anthryl groups. Heterocyclic aromatic groups are derived from hetero-aromatic compounds which are defined as in Kirk-Othmer, "Encyclopedia of Chemical Technology", Second Edition, Volume 2 (1963), page 702: obtained by replacement of one or more carbon atoms of a carbocyclic aromatic compound by a heteroatom selected from O or S—and also include those heterocyclic compounds having five-membered rings which show aromatic characteristics and are mentioned on page 703 of said volume. Optional substituents include one or more of halogen atoms having an atomic number of from 9 to 35, inclusive, or an alkyl, alkenyl or alkoxy group containing 1 to 6 carbon atoms, each optionally substituted by one or more halogen atoms, optionally substituted phenoxy, phenyl, benzyl or benzoyl and equivalent kinds of substituents. Illustrative examples of the optically-active alpha-hydroxynitriles include alpha-hydroxy-alpha-methylbutyronitrile, alpha-hydroxy-alpha-methylbenzeneacetonitrile, alpha-hydroxyisobutyronitrile and the like.

Preferably, the alpha-hydroxynitrile compound has the formula

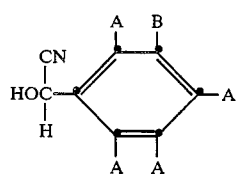

wherein each A is independently a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive; B is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive, or is a group

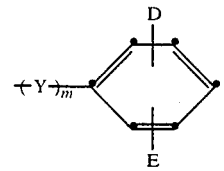

in which Y is O, $CH_2$, or $C(O)$; m is 0 or 1 and D and E each independently is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive.

Preferably, the (optically-active)alpha-hydroxynitrile can have the R- or S-configuration, and therefore, include either the R- or, preferably S-alpha-hydroxynitrile of the formula

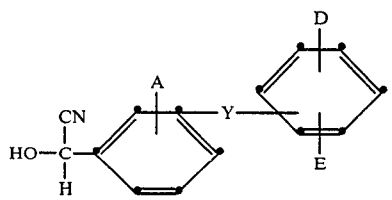

wherein Y is O, $CH_2$, or $C(O)$; each A, D and E independently is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive. Preferably, each A, D or E independently is a hydrogen atom, a fluorine atom, a chlorine atom, a methyl group, a trifluoromethyl group or a methoxy group. Preferably, one of D and E is a hydrogen atom. An especially preferred subclass of S-alpha-hydroxynitriles are those of the formula above in which D is a hydrogen atom and A and E each independently is a fluorine atom or a hydrogen atom, and, preferably, when either A or E is fluorine, each is located at the 4-position of the ring relative to the benzyl carbon when A or relative to the Y=O bearing carbon atom when E. Especially suitable alcohols are when A is a fluorine atom at the 4-position or a hydrogen atom and E is a hydrogen atom.

Examples of alpha-hydroxynitriles of the above formula include S-alpha-cyano-3-phenoxybenzyl alcohol, S-alpha-cyano-4-fluoro-3-phenoxybenzyl alcohol, S-alpha-cyano-3-(4-fluorophenoxy)benzyl alcohol, and their corresponding enantiomers.

The optically-active (chiral) tertiary amine catalyst is any optionally-substituted alkyl, cycloalkyl, aromatic or heterocyclic mono- or polyamine containing up to 40 carbon atoms (including polymers and copolymers and amine salts and the like), which will not interfere with the reaction. The amine is preferably a moderate to weakly basic amine. The optically-active amines, polymers and copolymers are conventional kinds of materials known in the art and can be prepared by known methods except for certain novel ketene reaction products discussed below. For example, numerous optically-active amines are specifically disclosed in Newman, P., "Optical Resolution Procedures for Chemical Compounds", Vol. 1, Amines and Related Compounds, Optical Resolution Information Center, Manhattan College, Riverdale, N.Y., Library of Congress Catalog Card No. 78-61452. This reference also discloses optically-active mono-, di- and polyamines which can be polymerized and co-polymerized by known procedures to form optically-active polymeric amines for use in the invention.

One embodiment of the optically-active tertiaryamine catalyst comprises a substituted optically-active amino acid which is preferably any acyclic, carbocyclic, aromatic or heterocyclic amino acid containing up to 20 carbon atoms, preferably up to 10 carbon atoms, additionally substituted by a moderate to weakly basic nitrogen base substituent or is the reaction product thereof with about one to about three moles of a ketene. Suitable nitrogen-base substituents include optionally substituted nitrogen-heterocyclic groups or amino groups, each optionally substituted by alkyl or cycloalkyl groups containing 1 to 6 carbon atoms or by optionally substituted phenyls. Other optional substituents include hydroxy, alkyl, alkoxy, amino, alkylthio, phosphoryloxy, amido and the like. Examples of nitrogen-heterocyclic groups include thiazolyl, imidazolyl, pyrrolyl, benzopyrrolyl and the like.

Non-limiting examples of the optically-active catalyst include beta-aminoalanine, ornithine, canavanine, anserine, kynurenin, mimosine, cystathionine, ephedrin, acylated ephedrins, histidinol, citrulline, carbamoylserine, cinchonine, quinine or acylated quinuclidinyl alcohols.

Another embodiment of the amine catalysts are the heterocyclic amines and polymers of heterocyclic amines. Non-limiting examples include di- and polyaziridines, polymers of acryloylcinchonines alone or with N,N-diacryloylhexamethylenediamine, di- and poly(iminoisobutylethylene), polymers of (N-benzyl-2-pyrrolidinylmethyl ester) with acrylate or a lower alkanoic acid, and like materials.

In another embodiment of the invention, the catalyst is an optically-active histidine-containing peptide; or is a histidine-containing di- or polypeptide; in which at least one of the histidinyl free N-H and free COOH groups is optionally modified with a protecting group into the form of an amide (or acid addition salt thereof) and an ester group, respectively; or the reaction product of one mole of a histidine or a histidine-containing di- or polypeptide with from about one mole to three moles of a ketene per mole of histidine group.

The di- or polypeptide is linear or cyclic. These peptides usually contain from about 2 up to about 16 peptide units, preferably 2 to 4 peptide units. Nitrogen-substituted amino acids, including these histidine-containing di- and polypeptides, are prepared by conventional peptide synthesis, for example, as in Greenstein, J. P. and M. Winitz, "Chemistry of the Amino Acids", John Wiley & Sons, Inc., New York, 1961.

The dipeptides of the histidine-containing catalyst are preferred, especially in the cyclic dipeptide form. The di- or polypeptides may also contain an alanine, and those prepared with alanine, phenylalanine, or alanine derivatives, are preferred.

In one embodiment of the invention, the asymmetric carbon atoms in the histidine-containing peptide is a catalyst in the D configuration, although the L-configuration in the histidine containing peptide is also useful. Choice of chirality in the catalyst can be made so as to provide the chirality desired in the product.

Functional groups in the amino acid catalyst can contain protecting groups; any conventional amino acid protecting group known in the art can be used. For example, the protecting group is an organic acid in the case of the free N-H or an alcohol in the case of the free COOH. Any organic acid and alcohol which will not interfere with the reaction can be used as the protecting group. Preferably, the protecting group is another amino acid. Any amino acid can be used, but, preferably, the amino acid is non-heterocyclic and is a monoamino or diamino-alkanoic or aralkanoic acid, such as alanine, phenylalanine, glutamic acid, glycine and the like.

Acid addition salts of the amine catalysts are formed with any acid that will not interfere with the reaction. Suitable inorganic acids include hydrohalogenic acids, such as hydrochloric or hydrobromic; sulfur acids, such as sulfuric or toluenesulfonic; and phosphorus acids, such as phosphoric or phenylphosphonic; and organic acids, such as oxalic acid and the like, are also suitable to form the salts.

When preparing the di- or polypeptide catalyst also having an alanine (containing moiety), it is prepared from alanine or its derivatives; this includes alanine, beta-aminoalanine, beta-phenylalanine, 3,4-dihydroxphenylalanine and the like. When preparing the catalyst from a histidine (containing moiety, including substituted histidines), it is preferably histidine, 3-methylhistidine, 1-methylhistidine, 1-ethylhistidine, 1-propylhistidine, or 1-benzylhistidine and the like. Very good results are obtained when 1-methylhistidine is the moiety. Preferably, the catalyst is a cyclic dipeptide containing a histidine moiety and an alanine moiety.

The peptide adducts (reaction produced) with ketene are novel and comprise another aspect of the invention. They are prepared to contain from about one mole to three moles of a ketene per mole of peptide and, preferably, about two and especially about one mole of ketene with a (cyclic) dipeptide. Obviously, it is preferable to form the adduct in situ with the non-symmetrical ketene reactant of the process, which is described below under process conditions. However, treatment of the optically-active catalyst with about 1:1 to 5 moles of a ketene, preferably in the absence of a solvent or any solvent used in preparing the ketene, is suitable. The ketene may also be a similar kind but symmetrical ketene, e.g. dimethyl ketene, diphenyl ketene or ketene itself.

Non-limiting examples of the optically-active histidine-containing catalyst include histidine, alpha-methylhistidine, 1-methylhistidine, cyclo(histidyl-histidine), (benzyloxycarbonylalanyl)histidine methyl ester, cyclo(alanyl-histidine), cyclo(beta-phenylalanyl-histidine), cyclo(beta-phenylalanyl-1-methylhistidine), cyclo(beta-phenylalanyl-3-methylhistidine), histidine methyl ester hydrochloride, histidine ethyl ester dihydrochloride, anserine, cyclo(valyl-histidine), glycyl-histidine, cyclo(phenylalanyl-glycyl-histidine), cyclo(leucylhistidine), cyclo(homophenylalanyl-histidine), cyclo(phenylalanylmethylhistidine), N-alpha-(beta-naphthoyl)histidine, histidyl-alanine, histidylphenylalanamide hydrochloride, histidyl-phenylalanine, cyclo(histidyl-proline), cyclo(glycyl-histidine) in free or protected form or a reaction product of these materials with a ketene. Also, cyclo(beta-phenylalanyl-histidine), cyclo(beta-phenylalanyl-1-methylhistidine) or cyclo(beta-phenylalanyl-3-methylhistidine) adduct with (4-(difluoromethoxy)phenyl)isopropylketene, histidine adduct with ketene, cyclo(glycyl-histidine) adduct with (4-(difluoromethoxy)phenyl)isopropylketene or histidyl-alanine adduct with dimethylketene and the like.

In one subclass of the invention, the peptide catalyst has the formula

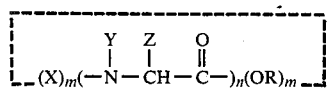

wherein X is H, alkyl or

each R is independently alkyl or cycloalkyl of up to 7 carbon atoms, optionally substituted phenyl, benzyl or the like, each of the n units of

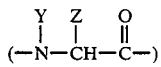

is independently substituted in which Y is hydrogen, acyl, alkyl, or aralkyl of up to 10 carbon atoms; Z is the residue of common amino acids that do not interfere in the process of the invention including benzyl, 3-carboxypropyl, 3-aminopropyl, mercaptomethyl, 4-hydroxybenzyl, imidazol-4-ylmethyl; each m is 0 or 1, n is 2 to 16; when each m is 0, the catalyst has a cyclic structure denoted by the dotted line; with the proviso that at least one histidine or substituted histidine unit is included in the catalyst; or reaction products of the above catalyst with one to three moles of ketene.

When the peptide catalysts are prepared by conventional methods in the presence of water, they can, if solid, also contain water of crystallization. The optically-active, nitrogen-based amino acid, e.g., histidine-containing peptide, catalyst of the invention, thus, includes the presence or absence of water of crystallization when solid.

Alternatively, the process of the invention comprises treating the non-symmetrical ketene as previously defined with an aldehyde or ketone and a source of cyanide ions in the presence of the optically-active catalyst previously defined.

Any aldehyde or ketone (carbonyl compound) is useful (provided it does not contain substituent groups that form other stable reaction products with cyanide ions or with the catalyst). Preferably, the aldehyde or ketone has the formula IV

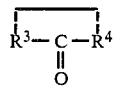   IV wherein $R^3$ is an optionally substituted hydrocarbyl or heterocyclic group and $R^4$ is an optionally substituted hydrocarbyl group or a hydrogen atom, or, alternatively, $R^3$ and $R^4$ together with the carbon atom to which they are attached form a carbocyclic group.

The hydrocarbyl groups represented by $R^3$ and $R^4$ in the formula IV may be, for example, an alkyl, a cycloalkyl or an aryl group of up to 20 carbon atoms, preferably up to 10 carbon atoms, or $R^3$ in the formula IV may be a carbocyclic or an O or S heterocyclic aryl group. Examples of carbocyclic aryl groups are phenyl, 1-naphthyl, 2-naphthyl and 2-anthryl groups. Heterocyclic aromatic groups are derived from hetero-aromatic compounds which are defined as in Kirk-Othmer, "Encyclopedia of Chemical Technology", Second Edition, Volume 2 (1963), page 702: obtained by replacement of one or more carbon atoms of a carboxylic aromatic compound by a heteroatom selected from O or S—and also include those heterocyclic compounds having five-membered rings which show aromatic characteristics and are mentioned on page 703 of said volume. Such aldehydes and ketone compounds are described in U.S. Pat. No. 4,132,728. Optional substituents include one or more of halogen atoms having an atomic number of from 9 to 35, inclusive, or an alkyl, alkenyl or alkoxy group containing 1 to 6 carbon atoms, each optionally substituted by one or more halogen atoms, or optionally substituted phenoxy, phenyl, benzyl or benzoyl and equivalent kinds of substituents.

Preferably, an aromatic aldehyde is used of the formula

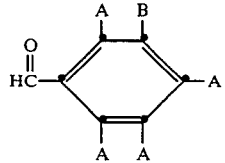

wherein each A is independently a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive; B is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive; or is a group

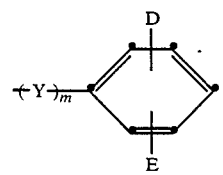

in which Y is O, $CH_2$, or C(O); m is 0 or 1 and D and E each independently is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive.

Preferably, an aldehyde is used corresponding to the alpha-hydroxynitrile previously defined and, thus, has the formula

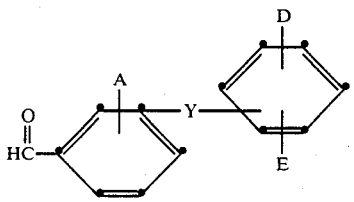

wherein A, D, E and Y have the same meanings as given in the formula above.

Examples of suitable aldehydes of the formula above include 3-phenoxybenzaldehyde, 4-fluoro-3-phenoxybenzaldehyde and the like.

The source of cyanide ions is hydrogen cyanide or agent which generates hydrogen cyanide, such as a simple alpha-hydroxynitrile such as acetone cyanohydrin, under the reaction conditions. The molar ratio of hydrogen cyanide to aldehyde or ketone is from about 1.0 to about 3.0 moles per mole of aldehyde or ketone and, preferably, from about 1.1 to about 2.0.

The preparation of the cyanomethyl esters is conducted by adding the non-symmetrical ketene to the alpha-hydroxynitrile, or to the aldehyde or ketone and a source of cyanide ions, dissolved in a solvent containing the optically-active, e.g., D-histidine-containing peptide catalyst, agitating the mixture, e.g., by stirring, and maintaining the reaction conditions for an amount of time to effect the formation of the optically-active ester. Separation and recovery of the optically-active ester product are achieved by conventional techniques, including extraction and the like.

The amount of catalyst can vary. For example, it can be used in the range of from about 0.01 to about 5 mole percent based upon the weight of the alpha-hydroxynitrile, aldehyde or ketone present, preferably about 0.1 to about 2.5 mole percent.

The molar ratio of the starting materials, non-symmetrical ketene and alpha-hydroxynitrile, aldehyde or ketone can vary. For example, the molar ratio of ketene to alpha-hydroxynitrile is from about 5:1 to about 1:5 and, preferably, from about 2:1 to about 1:2. However, it is desirable to have a molar excess of ketene to alpha-hydroxynitrile, aldehyde or ketone of from about 1:1.1 to about 1:1.5.

The temperature of the reaction as well as the pressure can vary. At normal pressures, the temperature is from about 10° C. to about 50° C., more or less. Ambient temperatures of about 0° C. to about 35° C. are convenient, and temperatures of about 0° C. to about 15° C. are preferred.

The alpha-hydroxynitriles and their corresponding aldehydes or ketones are generally known in the literature. They can be either directly synthesized chemically or often enzymetically or, in the case of optically-active alpha-hydroxynitrile, resolved by methods conventionally known in the art, including those described in U.S. Pat. Nos. 3,649,457 and 4,273,727, Oku et al., *J.C.S. Chem. Comm.*, pages 229–230 (1981) and Becker et al., *J. Amer. Chem. Soc.*, 88, pages 4299–4300 (1966) and the like.

The optically-active alpha-hydroxynitriles, particularly in the S-configuration, are prepared by treating the corresponding aldehyde or ketone with hydrogen cyanide in a solvent (such as hydrocarbon, ether and the like, preferably the same as used in the reaction of the product alcohol with the non-symmetrical ketene) and in the presence of a cyclo(D-phenylalanyl-D-histidine)- dipeptide catalyst. Such preparation of S-alpha-hydroxynitriles is disclosed and claimed in U.S. patent application Ser. No. 443,763, filed Nov. 22, 1982, which is incorporated by reference and discussed below.

The catalyst is prepared by conventional peptide synthesis, for example, as in Greenstein, J. P. and M. Winitz, "Chemistry of the Amino Acids", John Wiley & Sons, Inc., New York, 1961. They can be recovered by extraction with acid followed by neutralization with a base.

In one embodiment of the process for preparing optically-active alpha-hydroxynitriles from aldehydes or ketones, the catalyst comprising a solid cyclo(D-phenylalanyl-D-histidine) or cyclo(L-phenylalanyl-L-histidine) having a substantially non-crystalline component as claimed in co-pending U.S. Ser. No. 535,500, filed Sept. 26, 1983, and also described below.

In other words, the catalyst has a component having a substantially amorphous or non-crystalline structure. While the precise form of this cyclo(D-phenylalanyl-D-histidine) or cyclo(L-phenylalanyl-L-histidine)dipeptide is not known, it appears that in the activated (amorphous or non-crystalline) form, a number of the available —NH groups in the dipeptide are free of intermolecular hydrogen bonding to the available —C=O groups of the dipeptide crystal lattice as compared to the less active (crystalline component) form. This is believed to involve the formation of a less bonded linear or planar (or sheet) form of peptide structure as opposed to the highly bonded ribbon (or chain) form of peptide structure because of the increase in the number of —NH groups free of intermolecular hydrogen bonding to available —C=O groups in the dipeptide lattice. Such being the case, the degree of amorphousness or non-crystallinity as most readily determined by X-ray diffraction.

The wide-angle X-ray scattering (WAXS) measurements were carried out in reflection by means of a Philips APD3600/02 automated X-ray diffractometer. The samples were scanned at 20° C. in air from 5.0° to 60.0° $2\theta$ at 0.02 degree increments, and 0.6 second time increments with Cu K$\alpha$ radiation (40 KV, 35 ma).

The percent crystallinity was determined by a modified Hermans and Weidinger method (P. H. Hermans and A. Weidinger, *Makromol. Chem.*, 50, 98 (1961)). The diffuse background scattering below the main peaks was constructed assuming a linear between $5° \leq 2\theta \leq 60°$ and approximating the amorphous scattering with a smooth curve. The X-ray crystallinity, $W_c$, was calculated from the integrated crystalline and amorphous intensities $F_c$ and $F_a$ by the equation $W_c = F_c/(F_c + F_a)$. The various definitions can be found in the text H. P. Klug and L. E. Alexander, *X-Ray Diffraction Procedures for Polycrystalline and Amorphous Materials*, Wiley-Interscience, New York, (1974).

As used herein the terms "amorphous" or "non-crystalline" define active catalyst materials which have about 20% or more of an amorphous or non-crystalline component as determined by the area of the X-ray diffraction spectra obtained by the method described above. Preferably, the "amorphous" or "non-crystalline" component of the materials as defined by the X-ray diffraction spectra is about 45% to about 65% or higher. Preferably, the "amorphous" or "non-crystalline" component is about 65% or higher.

The catalysts are also analyzable by photomicrographs in which inefficient catalysts consist of agglomerates of fine crystallites. Crystallites are not evident in photomicrographs of active catalysts, which when, for example, are spray-dried, take the form of hollow-appearing spheres.

The solid catalyst can be recovered by extraction with acid followed by neutralization with a base or preferably by treating with (dissolving in) a solvent, for example a hydroxylic solvent, including lower alkanols of 1 to 10 carbon atoms such as isopropanol or preferably methanol (preferably with heating, e.g. to reflux or quick flash), and reprecipitating (preferably below ambient temperature) which produces a less crystalline (or more amorphous) catalyst structure.

While it is preferred to directly prepare the catalyst of the present invention having the non-crystalline component, it is also within the scope of this invention to prepare a substantially crystalline catalyst and to subsequently activate the catalyst by converting at least part of the crystalline material to an amorphous form. Thus, the present invention is directed to both a method of directly preparing an active cyclo(D-phenylalanyl-D-histidine) or cyclo(L-phenylalanyl-L-histidine)dipeptide catalyst and to a method of activating a crystalline catalyst of this type, which methods both involve reducing or preventing the formation of a substantially crystalline form thereof. In the case of activation of a crystalline catalyst, the crystalline form is first broken down and then prevented at least in part from reforming.

It is believed that the breakdown of or the prevention of the formation of a number of intermolecular bonds between the amino N—H and the carboxyl C=O groups in the crystal lattice makes the catalyst have an amorphous or non-crystalline form. In any event, an ordered deposition of crystals of the catalyst is discouraged or reduced.

Any means which will accomplish this reduction or prevention either during the catalyst preparation or an after treatment are within the scope of the invention. Among the illustrative examples of methods which reduce or prevent the formation of a highly crystalline form or highly ordered arrangement are (a) very rapid evaporation of a solution of the catalyst, in the presence or absence of impurities or crystallinity inhibitors; (b) rapid precipitation of the catalyst from solution by dilution in a poor solvent; (c) freeze drying of a solution of the catalyst; (d) rapid cooling of the melted catalyst in the presence or absence of impurities or crystallinity inhibitors; (e) use of crystallinity inhibitors during solidification; and the like.

The unactivated dipeptide catalyst, when recovered at the end of a conventional synthesis process, is often almost completely inactive in the cyanohydrination reaction, apparently because it has become highly crystalline as can be determined by X-ray diffraction. Activation, as used herein, appears to involve converting at least part of the normally crystalline material into an amorphous form such that the dipeptide is swelled by the reaction mixture and the chiral base function of the catalyst is made accessible to the reactants. In order to produce high chirality in the cyanohydrination product, it appears that the catalyst should preferably be essentially insoluble in the cyanohydrination solvent.

The first step in converting what is or what normally would be a crystalline material to an amorphous form is to break down (or prevent) formation of the intermolecular bonds in the crystal lattice. The breakdown readily occurs when the material is melted or dissolved in a solvent. Once this has been accomplished, a method is used that will allow the separation of the dissolved material from the solvent at a rate such that normal crystalline cannot occur. There are a number of ways in which this might be effected: (a) rapid evaporation of the solvent, e.g. as in a spray dryer; (b) rapid precipitation of the material by pouring a solution of it into a large volume of a different solvent that is miscible with the original solvent but does not dissolve, to a large extent, the material to be precipitated; (c) rapid freezing of a solution followed by sublimation of the solvent (freeze drying); (d) rapid cooling of the melted catalyst; and (e) use of inhibitors alone or with any of the above methods (a)-(b). Preferably, the method used is (a) rapid evaporation of the solvent and, especially, by means of spray drying.

Because of the polar nature and high melting point (~250° C.) of cyclo(D-phenylalanyl-D-histidine) or cyclo(L-phenylalanyl-L-histidine), the choice of solvents that will dissolve it to any appreciable extent is very limited. Potential solvents suitable and unsuitable that have been tested include those listed in Table 1 in order of decreasing effectiveness, and the use of these will be discussed below in relation to the method of catalyst activation via recovery techniques or specific subsequent activation treatment.

TABLE 1

| SOLVENTS TESTED FOR SOLUBILITY OF CYCLO(D-PHENYLALANYL-D-HISTIDINE) | | |
|---|---|---|
| Solvent | B.P./°C. | Solvency |
| Dimethyl Sulfoxide | 189 | Good (5–10% w) |
| Acetic Acid | 118 | Good |
| Formamide | 210 | >2.3% at 25° C. |
| 1-Methyl-2-pyrrolidinone | 202 | >2.2% at 25° C. |
| Dimethylformamide | 153 | Fair to Good, <5% at 90° C. |
| Liquid Ammonia | −33 | ~2% at −40° C. |
| N—methylformamide | 185 | >2.4% at 25° C. |
| Methanol | 64 | 1% w Hot, 0.3% w at 25° C. |
| Water | 100 | Fair to Poor, 0.1% at 25° C. |

The use of crystallization inhibitors is an alternative method of reducing or preventing the crystalline form of the dipeptide. Many chemicals can be used. It is useful if the crystallization inhibitor has a similar kind of structure or has one or more substituents similar in kind to those found in the dipeptide, but the inhibitor is not identical to the units of the dipeptide. In the case of this dipeptide, useful kinds of crystallization inhibitors include those materials containing a —N—H and/or —C=O group, including ureas, aldehydes and amines. Even by-product impurities of the dipeptide process containing such substituents are useful crystallization inhibitors, e.g. making an impure product can make a more active catalyst.

The amount of catalyst used in making the S-alpha-hydroxynitrile can vary. For example, it can be used in the range of from about 0.1 to about 10 mole percent based upon the weight of the aldehyde present, preferably about 1.0 to about 7.5 mole percent. The catalyst is preferably well dispersed in the reaction mixture.

When the catalysts are prepared by conventional methods in the presence of water, they can, if solid, also contain solvent (e.g. water) of crystallization. The optically-active, D-histidine-containing peptide catalyst of the invention used to prepare the optically-active alpha-hydroxynitrile thus includes the presence or absence of solvent (e.g. water) of crystallization when solid.

The non-symmetrical ketenes used to prepare the optically-active esters are generally known in the art or are novel. Ketenes used in the present invention can be prepared by treating the corresponding acid halide with a tertiary amine.

Suitable tertiary amines include alkyl, aryl or heterocyclic tertiary nitrogen base including mono- or polyamines and the like. Preferably, the tertiary amine is an amine in which any alkyl groups contain from 1 to 10 carbon atoms, any aryl or aralkyl groups contain from 6 to 20 carbon atoms and 1 to 2 hydrocarbyl rings, and any heterocyclic amines contain at least one ring nitrogen atom in a 5 or 6 membered heterocyclic ring optionally containing a sulfur or oxygen atom or another nitrogen atom, such as trimethylamine, triethylamine, tri-n-propylamine, pyridine and the like. Desirably, a tertiary amine contains three alkyl groups of 1 to 4 carbon atoms, for example: trimethylamine, tri-n-propylamine, and especially triethylamine or trimethylamine.

The reaction to prepare the non-symmetrical ketene is conducted in the presence or absence of a solvent. When a solvent is used the solvent is preferably a non-hydroxylic solvent such as hydrocarbons, chlorinated hydrocarbons, ethers and the like. For example, suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between 40° and 65° C., between 60° and 80° C. or between 80° and 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Suitable chlorinated hydrocarbons contain from 1 to 4 chlorine atoms in combination with an alkane chain containing from 1 to 4 carbon atoms or with a benzene ring, for example, carbon tetrachloride, chloroform, dichloromethane, 1,2-dichloroethane, trichloroethane, perchloroethane, chlorobenzene and 1,2- or 1,3-dichlorobenzene and the like. Ethers are generally those containing from 4 to 6 carbon atoms such as diethyl ether, methyl tert-butyl ether and diisopropyl ether and the like. Tetrahydrofuran and dioxane are also useful.

In the preparation of the non-symmetrical ketene, the molar ratio of the starting materials can be varied widely. For example, the molar ratio of acid halide to base is from about 10:1 to about 1:10, and preferably from about 5:1 to about 1:5. However, it is desirable to have a molar excess of base to acid halide. Therefore, a molar ratio of acid halide to base is desirably from about 1:1 to about 1:5 and conveniently from about 1:1.2 to about 1:2.

In the preparation of the non-symmetrical ketene, the temperature can be varied widely. At normal pressure, for example, the temperature of reaction can be varied but is preferably, for example, from about 10° C. to 40° C. more or less, although higher temperatures of up to about 75° C. to about 95° C. have been found very useful.

Separation and recovery of the product non-symmetrical ketene are achieved by conventional methods, including crystallization and the like.

This process of the invention is useful for preparing non-symmetrical ketenes from any acid halides which do not contain substituted groups which would react with the base. For example, the acid halide can be that of an acyclic, alicyclic, aromatic or heteroaromatic acid. Preferably, the acid halide has the formula V

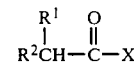

wherein X is the halogen atom, such as chlorine or bromine, $R^1$ and $R^2$ each independently is an alkyl, aralkyl, alkoxy, aryloxy, alkylthio, alkylsulfonyl, arylthio, or arylsulfonyl group containing from 1 to 10 carbon atoms or a cycloalkyl group containing 3 to 7 ring carbon atoms, or when taken together with the carbon atom to which they are attached form a non-symmetrical cycloalkyl group containing 4 to 7 ring carbon atoms; $R^2$ is also an alkenyl or alkynyl containing from 2 to 10 carbon atoms; a naphthyl group; a phenyl group; a heterocyclic group containing 5 or 6 ring atoms, one of which is oxygen, sulfur or nitrogen, and the remainder are carbon atoms, or is an amino group disubstituted by acyl, alkyl containing up to 10 carbon atoms, or a phenyl group. The $R^1$ and $R^2$ groups can be optionally substituted by one or more of halogen of atomic numbers 9 to 35, an alkyl, haloalkyl or cycloalkyl group containing up to 7 carbon atoms, alkenyl or haloalkenyl group of 2 to 4, haloalkoxy or alkoxy group of 1 to 4 carbon atoms, haloalkylthio or alkylthio group of 1 to 4 carbon atoms or equivalent kinds of substituents.

One class of acid halides are halides of pyrethroid acids, including those of U.S. Pat. Nos. 4,062,968 and 4,199,595. Examples of such acid halides include those having the formula V in which $R^1$ is isopropyl or cyclopropyl, optionally substituted by one or more chlorine atoms; $R^2$ is an alkyl group containing 1 to 6 carbon atoms; an alkenyl group containing 2 to 6 carbon atoms; a naphthyl group, a phenyl group or a (benzyloxycarbonyl)phenylamino group, each optionally ring-substituted by one or more of halogen, alkyl, haloalkyl, alkoxy or haloalkoxy in which the halogens are bromine, chlorine or fluorine and the alkyl groups contain 1 or 4 carbon atoms. For example, the acid halide is isopropyl(4-chlorophenyl)acetyl chloride, isopropyl(4-(difluoromethoxy)phenyl)acetyl chloride, isopropyl((4-trifluoromethyl)-3-chlorophenyl)(benzyloxycarbonyl)amino)acetyl chloride, and the like.

Preferably, in formula V, $R^1$ is isopropyl and $R^2$ is a phenyl group optionally substituted by halogen, an alkyl or haloalkyl group of 1 to 4 carbon atoms or an alkoxy or haloalkoxy group containing 1 to 4 carbon atoms, preferably at the para position, especially useful are 4-chlorophenyl, 4-(difluoromethoxyphenyl), 4-methylphenyl, 4-tert-butylphenyl and the like.

Many of the non-symmetrical ketenes of the invention are known in the art per se, for example, (4-chlorophenyl)isopropylketene, as in U.S. Pat. No. 4,199,527. Some other non-symmetrical ketenes are believed to be novel, for example, including (4-(difluoromethoxy)phenyl)isopropylketene.

The cyanomethyl esters for which the optically-active form is prepared by the process of the invention, i.e. of formula I

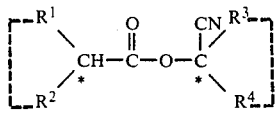

are generally known in the art, including from Francis et al., *J. Chem. Soc.*, 95, pages 1403–1409 (1909) and the like, and in the optical forms, including U.S. Pat. Nos. 4,151,195, 4,239,737, 4,328,167 and 4,133,826, and British Pat. No. 2,014,137 and the like. Any of the alpha-cyanomethyl esters prepared can be hydrolyzed to their corresponding acids by conventional hydrolysis methods known in the art. Preferably, the product optically-active ester is S-alpha-cyano-3-phenoxybenzyl S-alpha-isopropyl-p-chlorophenylacetate, S-alpha-cyano-3-phenoxybenzyl S-alpha-isopropyl-p-(difluoromethoxy)-phenylacetate, and the like.

ILLUSTRATIVE EMBODIMENTS

Embodiment 1

N-(Benzyloxycarbonyl)-D-phenylalanine

A 15.0 g sample of D-phenylalanine was dissolved in 45 ml of aqueous solution containing 7.26 g of 50% sodium hydroxide. This solution was stirred at 0°–10° C. as 16.3 g of benzyl chloroformate was added rapidly in portions. The resulting reaction was mildly exothermic, and shortly after addition, solids precipitated. An additional 45 ml of water and 3.63 g of 50% sodium hydroxide were added, causing most of the solids to redissolve. The reaction mixture was stirred for 20 minutes and then acidified with 6N hydrochloric acid. The resulting solids were filtered, washed with water and then with hexane, and dried by suction and then under vacuum to give 47 g of white solids. These solids dissolved in ether were washed twice with 1N hydrochloric acid and then with water, dried over $MgSO_4$ and stripped to 35° C. at 2.5 mm Hg to give 27.7 g of the desired product as a colorless oil.

Embodiment 2

N-(Benzyloxycarbonyl)-D-phenylalanine, p-nitrophenyl Ester

A 300 ml three-neck flask with stirrer and dropping funnel was charged under a nitrogen atmosphere with 27 g of the acid of Embodiment 1 above in 135 ml of pyridine, followed by 13.2 g of p-nitrophenol. The resulting solution was cooled to 0° to 10° C. as 14.6 g of phosphorus oxychloride was added. The resulting mixture was warmed to 25° C., stirred for 15 minutes, then poured into 300 ml of ice water. Filtration of the resulting solid, followed by washing with water and drying by suction, gave 33 g of product. This was crystallized from 340 ml of hot ethyl alcohol with chilling to −5° C. The product was filtered, washed with chilled ethyl alcohol, then with hexane, and sucked dry to give 28.7 g of the desired product, m.p. 122.5°–124.5° C., $[\alpha]_D^{23}+24.7$ (c 2.0, dimethylformamide).

Embodiment 3

N-Benzyloxycarbonyl-D-phenylalanyl-D-histidine Methyl Ester

To a stirred solution of 5.0 g of D-histidine methyl ester hydrochloride in 40 ml of methylene chloride was added 4.18 g of triethylamine followed by 8.27 g of the nitrophenyl ester prepared as in Embodiment 2 above. The reaction mixture immediately became bright yellow and solids began to precipitate. The reaction mixture was stirred for 2 hours, then stored overnight at −10° C. The reaction mixture was rewarmed to room temperature, and 0.6 ml of triethylamine was added. Then, 490 mg of the D-histidine methyl ester hydrochloride was added, and stirring was continued for 2 hours. The reaction mixture was washed with 20 ml of water, then twice with 20 ml of 10% ammonium hydroxide, and then twice with 20 ml of water. All the washes were back-extracted serially with 20 ml of methylene chloride, and the combined organic phases were dried with $MgSO_4$ and stripped to 100 ml, filtered through silica, followed by 25 ml of 20% methanol in ethyl acetate. The resulting eluate was stripped to 40 ml and diluted to 120 ml with diethyl ether; the precipitated solid was filtered, washed with diethyl ether, and dried by suction to give 5.66 g of the desired product as a white solid, m.p. 114.5°–117° C. $[\alpha]_D^{20}-55.5$ (c 2 in $CHCl_3$).

Embodiment 4

Cyclo(D-phenylalanyl-D-histidine)

5.60 g of methyl ester of Embodiment 3 above was stirred and hydrogenated in 100 ml of methanol over 220 mg of 10% palladium on carbon at atmospheric pressure. After 3 hours, solids began to precipitate; an additional 25 ml of methanol was added to facilitate stirring. After 7 hours, an additional 280 ml of methanol was added as the mixture was heated to reflux. The mixture was filtered hot, and the filtrate was stripped to a gel-mush and mixed with 100 ml of diethyl ether. The resulting solid was filtered, washed with diethyl ether, and dried by suction and then under high vacuum at 35° C. to give 3.29 g of the desired product as an off-white powder, $[\alpha]_D^{23}=+68.5$ (c 2.0 in $CH_3COOH$).

Embodiment 5

(4-Chlorophenyl)isopropylketene

To a solution of 2.31 g of isopropyl(4-chlorophenyl)acetyl chloride in 10 ml of methylene chloride was added in one portion 1.5 g of triethylamine. After 18 hours, 15 ml of heptane was added to the mixture and the triethylamine hydrochloride was removed by filtration. The filtrate was stripped and 10 ml of heptane was added and the resulting mixture was filtered and stripped to give a yellow residue, which was dissolved in 5 ml heptane for GLC analysis. The resulting solution was distilled through a Bantam-ware short-neck head from an oil bath at 125°–150° C. and head temperature of 110°–100° C. at 0.2–0.05 mm to give 0.95 g of distillate and 0.81 g of gum. The distillate was crystallized twice from 2 volumes of hexane at −80° C. The solid was melted and stripped to about 40° C. at 0.5 mm to give 0.42 g of the desired product as a yellow liquid.

Embodiment 6

(4-Chlorophenyl)isopropylketene

A sample of 53.2 g of isopropyl(4-chlorophenyl)acetic acid was treated with 21.5 ml of thionyl chloride in a 500 ml flask and heated slowly to 80° C. and maintained at 80° C. for 20 minutes. The reaction mixture was allowed to stand at room temperature for 2 days. The volatiles were stripped to 75° C. at 0.5 mm Hg. The resulting yellow liquid was diluted with 250 ml of methylene chloride followed by addition of 38.0 g of triethylamine. The mixture was stirred until triethylamine hydrochloride began to precipitate after 30 minutes. After 16 hours, the reaction mixture was filtered and solid triethylamine hydrochloride was washed with heptane. Most of the solvent was stripped from the filtrate by rotary evaporation at 50° C. The residue was diluted with 75 ml of heptane and additional triethylamine hydrochloride was removed by filtration as above. The filtrate was restripped and rediluted with 75 ml heptane and refiltered with the aid of 25 ml of heptane. The filtrate was cooled in dry ice, seeded and crystallized. The resulting crystals were filtered with a filter stick and washed with chilled heptane. The filtered solids were melted, diluted with one-half volume heptane, crystallized at −80° C. and the collected solid was melted and stored at −80° C. The filtrate solution was warmed, stripped of most solvent, then distilled through a Bantam ware short path head at 0.05 to 0.06 mm Hg from an oil bath at 90°-120° C. Total distillate was 14.5 g collected as a bright yellow-orange liquid at a head temperature of 60°-85° C. The distillate was crystallized from an equal volume of pentane at −80° C., filtered and washed twice with heptane as above to give, on warming, a second melt. The stripped filtrates totalling 5.79 g were crystallized as above in a 6-inch test tube and the melt was recrystallized immediately as described above to give a third melt. The three melts were combined and stripped to 50° C. at 5 mm Hg to give 29.4 g of the desired ketene as a yellow liquid.

Embodiment 7

(4-Chlorophenyl)isopropylketene

To 57.75 g of isopropyl(4-chlorophenyl)acetyl chloride was added 69.4 ml of triethylamine. The mixture was allowed to stand overnight at 20° C. The resulting mushy solid was crushed, diluted with 300 ml of redistilled hexane and filtered. The solids were washed three times with 75 ml of hexane, filtered and dried by suction with calcium chloride dried air to give 32 g triethylamine hydrochloride. The combined hexane solutions of ketene slowly deposited additional solids; the mixture was let stand at room temperature overnight with the flask wrapped in aluminum foil and filtered again to give 0.75 g of additional solids. The solvent was removed from the filtrate by rotary evaporation, then taken briefly to 1 mm Hg. To the mixture was added 500 ml of hexane, and after filtration, the filtrate was stripped to a yellow oil. This oil was distilled through a Bantam-ware short path head at 0.5 mm Hg to give 28.61 g of the desired ketene as a yellow liquid, $d^{20}$ 1.10.

Embodiment 8

(4-(Difluoromethoxy)phenyl)isopropylketene

Following procedures similar to those described in Embodiment 7 above, the desired product is prepared by treating isopropyl(p-(difluoromethoxy)phenyl)acetyl chloride with triethylamine.

Embodiment 9

S-alpha-Cyano-3-phenoxybenzyl Alcohol

A 100 ml three-neck Bantam-ware flask was charged with 43 mg of cyclo(D-phenylalanyl-D-histidine) and put under a nitrogen atmosphere. Then, 3.51 ml of hydrogen cyanide was added by syringe causing the catalyst to swell and become a gel. After 5 minutes, 30 ml of toluene was added, causing additional catalyst to precipitate. 5.95 g of 3-phenoxybenzaldehyde was added all at once. The reaction mixture was stirred for 4.75 hours and then quenched with 20 ml of water containing 10 drops of concentrated hydrochloric acid. The toluene solution was separated, washed twice with water, and diluted to 50 ml with toluene for analysis, which showed 80% S-alpha-cyano-3-phenoxybenzyl alcohol isomer was produced.

Embodiment 10

S-alpha-Cyano-3-phenoxybenzyl Alcohol

The reaction of Embodiment 5 above was repeated using 171 mg of cyclo(D-phenylalanyl-D-histidine). At intervals, 0.25 ml samples were removed and examined by gas liquid chromatography as follows:

| Time | % Conversion of Aldehyde |
| --- | --- |
| 35 minutes | 20 |
| 2 hours | 76 |
| 6.5 hours | 95 |

After 7 hours, the reaction mixture was quenched by addition of 10 ml of 1N hydrochloric acid. The organic phase was separated and washed twice with water, dried over MgSO$_4$, filtered and stored at −10° C. The filtrate was diluted to 50 ml with toluene and the optical rotation was determined to be −1.54° at 21° in 1 dm cell. A sample of the product was acetylated with p-nitrophenylacetic anhydride and the stereoisomer ratio was determined by HPLC on a chiral Pirkle column to be 71% S-alpha-cyano-3-phenoxybenzyl alcohol and 29% R-alpha-cyano-3-phenoxybenzyl alcohol.

Embodiment 11

S-alpha-Cyano-3-phenoxybenzyl Alcohol

Two small round-bottom flasks having magnetic stirrers and septum covers were each charged with 22.5 mg of cyclo(D-phenylalanyl-D-histidine) and put under nitrogen. A sample of 0.98 ml of hydrogen cyanide was diluted to 25 ml with toluene and 5 ml of the solution was added via syringe to each flask. After about 5 minutes, 0.87 ml of 3-phenoxybenzaldehyde (POAL) was added to each flask. Flask No. 1 was stirred in an oil bath at 35° C. and flask No. 2 was stirred in a water bath at 24°-26° C. The results of these experiments are below.

| Time, | Flask No. 1 | | | Flask No. 2 | | |
|---|---|---|---|---|---|---|
| hr | POAL, % | α-Hydroxy-nitrile, % | R/S | POAL, % | α-Hydroxy-nitrile, % | R/S |
| 0.5 | 19 | 81 | 8.7/91.3 | 18 | 82 | 15.8/84.2 |
| 1 | 12 | 88 | — | 13 | 87 | 14.4/85.6 |
| 2 | 12 | 88 | — | 12 | 88 | — |
| 4 | 10 | 90 | 11.4/88.6 | 12 | 88 | 19.0/81.0 |
| 8 | 10 | 90 | — | 13 | 87 | — |

Embodiment 12

S-alpha-Cyano-3-phenoxybenzyl Alcohol

A reaction was conducted by contacting 0.0099 m/kg cyclo(D-phenylalanyl-D-histidine) with 0.99 m/kg of 3-phenoxybenzaldehyde followed by 2.2 m/kg of hydrogen cyanide and 190 ppm water. The reaction was conducted in toluene at 25° C. The product obtained with 93% conversion of aldehyde was 88% S-alpha-cyano-3-phenoxybenzyl alcohol isomer.

Embodiment 13

S-alpha-Cyano-3-phenoxybenzyl S-Isopropyl(4-chlorophenyl)acetate

A 1 dram vial was charged with 1 ml of a solution of alpha-cyano-3-phenoxybenzyl alcohol having an R/S ratio of ca 72/28, and 0.121 ml of (4-chlorophenyl)isopropylketene. Then, 7.5 mg of cyclo(D-phenylalanyl-D-histidine) was added. The reaction mixture was stirred at ambient temperature for 24 hours to give a colorless product containing a white, insoluble floc. The reaction product was centrifuged to remove solids, washed with 1N hydrochloric acid and twice with water, dried with MgSO₄ and filtered and diluted to 2 ml with solvent for analysis. The desired product had by Pirkle column analysis a ratio of 55.1% S-alpha-cyano-3-phenoxybenzyl S-isopropyl(4-chlorophenyl)acetate and 16.6% R-alpha-cyano-3-phenoxybenzyl R-isopropyl(4-chlorophenyl)acetate.

Embodiment 14

S-alpha-Cyano-3-phenoxybenzyl S-Isopropyl(4-chlorophenyl)acetate

A 1 dram vial was charged with 1 ml of S-alpha-cyano-3-phenoxybenzyl alcohol solution as described in Embodiment 13 followed by 0.121 ml of (4-chlorophenyl)isopropylketene and then 7.5 mg of cyclo(D-phenylalanyl-D-histidine). The resulting mixture was stirred at ambient temperature for 20 hours to give a colorless product liquid containing a white floc. This reaction product mixture was centrifuged and the insoluble cake of gel was washed and centrifuged 4 times with 1 ml portions of hexane. The combined organic extracts were washed with dilute hydrochloric acid and water, dried, stripped to below 1 ml and then diluted to 2 ml in toluene. The desired product had by Pirkle column analysis a ratio of 63.0% S-alpha-cyano-3-phenoxybenzyl S-isopropyl(4-chlorophenyl)acetate and 12.5% R-alpha-cyano-3-phenoxybenzyl R-isopropyl(4-chlorophenyl)acetate.

Embodiment 15

S-alpha-Cyano-3-phenoxybenzyl S-Isopropyl(4-chlorophenyl)acetate

The catalyst gel recovered from Embodiment 14 above was washed with 1.5 ml of hexane and charged to a 1 dram vial. The vial was charged with 1 ml of S-alpha-cyano-3-phenoxybenzyl alcohol solution as described in Embodiment 14 and 0.121 ml of (4-chlorophenyl)isopropylketene. The reaction mixture was stirred for 16 hours and then extracted 5 times with 1 ml hexane, and the combined extracts was stripped and diluted to 2 ml in toluene for analysis. The desired product had by Pirkle column analysis a ratio of 62.4% S-alpha-cyano-3-phenoxybenzyl S-isopropyl(4-chlorophenyl)acetate and 14.1% R-alpha-cyano-3phenoxybenzyl R-isopropyl(4-chlorophenyl)acetate.

Embodiment 16

S-alpha-Cyano-3-phenoxybenzyl S-isopropyl(4-chlorophenyl)acetate

A 0.5 dram vial containing a magnetic stirring bar and 4 mg of cyclo(D-phenylalanyl-D-histidine) was filled with nitrogen and capped with a septum cap. Into this vial was injected 0.174 ml of 3-phenoxybenzaldehyde followed by 0.044 ml of hydrogen cyanide. After 5 minutes stirring, 0.18 ml of (4-chlorophenyl)isopropylketene was added. After 2 days, the reaction mixture was diluted with toluene, washed with 1N hydrochloric acid, water, dried (MgSO₄) and filtered. A solution thereof in 1 ml toluene was analyzed and determined to be enriched in the desired material.

Embodiment 17

A Niro Atomizer laboratory spray dryer with a ca 31 inch diameter chamber was assembled. In operation, 40 SCFM N₂ is heated to 140° C. and fed to the dryer chamber. A warm solution of 0.5–1.0% w cyclo(D-phenylalanyl-D-histidine) in methanol is fed via a rotary vaned atomizer to the chamber above the N₂ inlet. The droplets of cyclo(D-phenylalanyl-D-histidine) solution are rapidly dried to give hollow spherical particles of 1 to 10 μm diameter. The combined stream is fed to a cyclone where 50–70% of the particles are captured.

Six test runs were made using 5 to 10 gm of cyclo(D-phenylalanyl-D-histidine) each. Starting with a catalyst that was inefficient for cyanohydrination, all the products were activated to give good reaction rate and produce (S)-alpha-cyano-3-phenoxybenzyl alcohol with EE's between 75–80% at 97% conversion of 3-phenoxybenzaldehyde. Water and sodium chloride, simulating recycle operation, apparently had no effect on activation. On the other hand, the addition of urea to further disrupt crystallization of cyclo(D-phenylalanyl-D-histidine) did not result in any further improvement. The results of the six test runs are tabulated in Table 2.

Following procedures similar to those described in Embodiment 17 above, cyclo(L-phenylalanyl-L-histidine) is activated by spray drying.

TABLE 2
ACTIVATION OF CYCLO(D-PHENYLALANYL-D-HISTIDINE) FOR SPRAY DRYING

| Experiment | Catalyst Purity % w | Feed Composition (Rest MeOH) DDCAT[d] % w | H₂O % w | NaCl % w | Others % w | Feed Rate ml/min | N₂ Rate SCFM[f] | Temp In °C. | Temp Out °C. | Atomizer RPM × 10⁻³ | Catalyst Recovery % | Particle Size μm | Cyanohydrination In Toluene at 25° C. Time hr | POAL[e] Conversion % | (S)—POAL.CN[e] Selectivity[c] % |
|---|---|---|---|---|---|---|---|---|---|---|---|---|---|---|---|
| 1 | 87 | 0.49 | | | | 115 | 42 | 135 | 60–75 | 37 | 46 | 1–12 | 1<br>2<br>4<br>5.5 | 92.2<br>95.9<br>96.9<br>95.9 | 91<br>90<br>90<br>90 |
| 2 | 87 | 0.48 | | | | 225 | 42 | ~160 | 60–70 | 31 | 58 | 1–12 | 1<br>3<br>4<br>5.1 | 91.3<br>95.5<br>96.7<br>98.4 | 90<br>88<br>88 |
| 3 | 92[b] | 0.84 | | | | 125 | 43 | 135–140 | 55–65 | 37 | 66[a] | 1–10 | 1<br>2<br>3<br>4 | 93<br>96.7<br>96.6<br>97.6 | 90<br>90<br>92<br>90 |
| 4 | 92[b] | 0.63 | 4.5 | | | 110 | 43 | 139 | 65–75 | 36 | 56[a] | 1–10 | 1<br>2<br>3 | 94.6<br>96.9<br>98.7 | 90<br>89 |
| 5 | 92[b] | 0.62 | 4.5 | 1.0 | | 135 | 43 | 137–140 | 55–65 | 36 | 68 | 1–10 | 1<br>2<br>3<br>4<br>5 | 93.6<br>96.6<br>95.4<br>97.5 | 91<br>90<br>91<br>90<br>90 |
| 6 | 92[b] | 0.65 | — | — | 0.033 | 125 | 43 | 139 | 70–75 | 36 | 58 | 1–10 | 1<br>2<br>4<br>5 | 92.3<br>91.0<br>94.7<br>96.0 | 90<br>90<br>89<br>90 |
| 7 | 92[b] | 0.80 | — | — | — | 135 | 42 | 135–140 | 55–70 | 38 | 77 | 1–10 | 1<br>2<br>3<br>4<br>5 | 93.3<br>96.1<br>95.9<br>97.6<br>96.0 | 93<br>91<br>92<br>92<br>91 |

[a]Mostly held in cyclone by static electricity.
[b]96% purity by pot. titration.
[c]EE = 2 (selectivity) − 100, %.
[d]DDCAT = cyclo(D-phenylalanyl-D-histidine)
[e]POAL = 3-phenoxybenzaldehyde, (S)—POAL.CN = (S)—α-cyano-3-phenoxybenzyl alcohol.
[f]SCFM = standard cubic feet per minute.

Embodiment 18

Table 3 summarizes the results of tests and scale-up experiments to activate the cyclo(D-phenylalanyl-D-histidine) catalyst by solvent evaporation, most of which were from methanol. Whereas the catalyst recovered by conventional crystallization was not very active, rapid evaporation of methanolic solutions was rather effective in producing active catalysts (Experiments 1-11). The addition of small amounts of impurities (5-10% basis catalyst) appeared to help prevent normal crystallization (compare Experiment 1, having no impurity, to those following it in the table). Except for dimethyl sulfoxide, all of the additives gave better results than the base case. These experiments involved rapid stripping of 25 ml of methanol from 0.2 g of catalyst in a rotating evaporator. Attempts to scale up Experiment 9 were only partially successful. The product from the first experiment had an activity/enantiomeric excess of 88%/75%, as compared to 98%/88% in the smaller experiment. The second of the large experiments was even less active, 75%/47%. Longer times required to strip off large volumes of solvent resulted in greater amounts of crystallization of the dipeptide, thus resulting in a less active material. A solution to this problem is to spray dry the solution so that the solids are recovered rapidly. Solvents that may be useful in this approach are methanol, liquid ammonia, and acetic acid.

Embodiment 19

Solvent precipitation is another way of activating the cyclo(D-phenylalanyl-D-histidine) dipeptide, and Table 4 summarizes some results using this approach. In all but one example shown, dimethyl sulfoxide (DMSO) was used to dissolve the catalyst as a 5% solution, and the dipeptide was precipitated by pouring this solution into a well-stirred vessel of second solvent, under a variety of conditions. In most cases, the precipitated catalyst formed a voluminous gel which was rinsed with the second solvent to remove dimethyl sulfoxide and blown dry. In Experiments 5-14 urea (5% basis catalyst) was added to the DMSO solution to aid in preventing crystallization of the dipeptide. In any case, from the results shown, it appears that (a) of the five precipitating solvents tested, dichloromethane and toluene appeared to be best; (b) high temperature (80° C.) gave better results than lower temperature (25° C.); (c) high dilution gave a better result than lower dilution (compare Experiments 5 and 6); and (d) the catalyst precipitated from liquid ammonia solution (Experiment 4) was moderately active (82% conversion in 3 hours) and quite selective (84% EE, even after 22 hours of contact with the catalyst). Unlike all of the others this product was a dense solid that was easy to filter and wash. A number of solvents for cyclo(PHE-HIS) shown in Table 1 can be used in this approach, namely, DMSO, acetic acid, formamide, 1-methyl-2-pyrrolidinone, dimethylformamide, N-methylformamide, liquid ammonia, and the like.

TABLE 3
ACTIVATION OF CYCLO(D-PHENYLALANYL-D-HISTIDINE) BY SOLVENT EVAPORATION

| | | | Cyanohydrination[a] | |
|---|---|---|---|---|
| Experiment | Method of Evaporation | Temp °C. | Conversion %/3 Hr | Enantiomeric Excess, % |
| 1 | Rapid small[b] evap. from methanol | ~0 | 83 | 79 |
| 2 | Rapid small evap. from methanol, +5% urea | ~0 | 96 | 87 |
| 3 | Rapid small evap. from methanol, +10% 3-phenoxybenzaldehyde | 0-20 | 95 | 85 |
| 4 | Rapid small evap. from methanol, +10% M acetic acid | 0-20 | 99 | 85 |
| 5 | Rapid small evap. from methanol, +10% $CH_3CN$ | 0-20 | 99 | 86 |
| 6 | Rapid small evap. from methanol, +10% α-isopropyl-p-chlorophenyl-acetonitrile | 0-20 | 97 | 87 |
| 7 | Rapid small evap. from methanol, +7% HIS—OME/triethylamine | 0-20 | 95 | 75 |
| 8 | Rapid small evap. from methanol, +50% water | 0-20 | 92 | 80 |
| 9 | Rapid small evap. from methanol, +5% filtrate residue | 0-20 | 98 | 88 |
| 10 | Rapid small evap. from methanol, +10% dimethyl sulfoxide | 0-20 | 16 | 31 |
| 11 | Rapid small evap. from methanol, +5% Z—D-PHE—HIS—OME | 0-20 | 96 | 87 |
| 12 | Slow Evaporation from hot methanol/water | 70-90 | 67 | 63 |
| 13 | Large run similar to 9 (15 g) | | 88 | 75 |
| 14 | Large run similar to 9 (15 g) | | 75 | 47 |
| 15 | Medium run similar to 9 (7 g in 2 Hr) | | 98 | 86 |

[a]Cyanohydrination of 3-phenoxybenzaldehyde with HCN to give (S)—alpha-cyano-3-phenoxybenzyl alcohol.
[b]Small means 0.2 g of catalyst in 25 ml of solvent.

TABLE 4

ACTIVATION OF CYCLO(D-PHENYLALANYL-D-HISTIDINE) BY SOLVENT PRECIPITATION

| | | Cyanohydrination[d] | |
|---|---|---|---|
| Experiment | Method of Precipitation | Conversion %/3 Hr | Enantiomeric Excess, % |
| 1 | From dimethyl sulfoxide (5%) into diethyl ether | 65 | 41 |
| 2 | From dimethyl sulfoxide (5%) into toluene, 80° C. | 97 | 72 |
| 3 | From dimethyl sulfoxide (5%) into toluene 25° C., large scale | 74 | 37 |
| 4 | From liquid $NH_3$ (2%) into diethyl ether, $-40°$ C. | 82 | 84[b] |
| 5 | From dimethyl sulfoxide[a] into 20 V toluene, 25° C. | 42 | 31 |
| 6 | From dimethyl sulfoxide into 5 V toluene, 25° C. | 4 | 10 |
| 7 | From dimethyl sulfoxide into 20 V toluene, 80° C. | 85 | 57 |
| 8 | From dimethyl sulfoxide into 20 V acetonitrile, 80° C./25° C. | 77 | 37[e] |
| 9 | From dimethyl sulfoxide into 20 V acetonitrile, 25° C. | 2 | 18[f] |
| 10 | From dimethyl sulfoxide into 20 V tetrahydrofuran, 25° C. | 2 | 19[g] |
| 11 | From dimethyl sulfoxide into 20 V diethyl ether, 25° C. | 2 | 0[c] |
| 12 | From dimethyl sulfoxide into 20 V dichloromethane | 77 | 49 |
| 13 | From dimethyl sulfoxide into 20 V tetrahydrofuran + 1% v/v $H_2O$, 25° C. | 77 | 60 |
| 14 | Experiment 13 and vacuum oven dried | 89 | 50[h] |

[a]Catalyst 5% w/v in dimethyl sulfoxide, urea 5% basis catalyst.
[b]After 22 hours at 95% conversion.
[c]After 71 hours the enantiomeric excess was 24% at a conversion of 97%.
[d]Cyanohydrination of 3-phenoxybenzaldehyde with HCN to give (S)—alpha-cyano-3-phenoxybenzyl alcohol.
[e]At 92% conversion.
[f]At 44% conversion.
[g]At 49% conversion.
[h]After 4 hours.

Embodiment 20

Another method tested for activating the catalyst is freeze drying. This approach requires a solvent for the dipeptide that freezes at a convenient temperature and is volatile enough to be sublimed at below that temperature and at a practical pressure (vacuum). Of the solvents tested, only water and acetic acid meet these requirements. The results of some of these tests are summarized in Table 5. Freeze drying of a 0.1% w solution of the dipeptide in water gave an excellent product (Experiment 5). An attempt to freeze dry a solution in dimethyl sulfoxide failed because the solvent was too high boiling to be sublimed at about 0° C. and 170 microns pressure. On the other hand, solutions in glacial acetic acid were readily freeze dried. The products from this freeze drying contains one mole of acetic acid per mole of catalyst. In spite of this, the product was surprisingly active and selective (Experiment 2). This acid is relatively loosely held by the catalyst, and it was volatilized away in a sweep of air, on the one hand (Experiment 3), or neutralized by triethylamine treatment, on the other (Experiment 4). In both cases the products had about the same activity/selectivity: 93%/72%.

TABLE 5

ACTIVATION OF CYCLO(D-PHENYLALANYL-D-HISTIDINE) BY FREEZE DRYING

| | | Cyanohydrination[c] | |
|---|---|---|---|
| Experiment | Solvent/Work Up | Conversion %/3 Hr | Enantiomeric Excess, %[b] |
| 1 | From 2% solution in dimethyl sulfoxide | — | — |
| 2 | From 1.9% solution in acetic acid | 74 | 56 (6.5) |
| 3 | Product from experiment 2 air swept 2 days | 93 | 73 (5) |
| 4 | Product from Experiment 2 treated with triethylamine in diethyl ether | 93 | 72 (6.3) |
| 5 | From 0.1% solution in water | 98 | 85 (2.5) |

[a]Solution frozen at $-40°$ C.; solvent sublimed at 0.1 Torr.
[b]Numbers in parentheses indicate time, in hours.
[c]Cyanohydrination of 3-phenoxybenzaldehyde with HCN to give (S)—alpha-cyano-3-phenoxybenzyl alcohol.

Following procedures similar to those described in Embodiment 21 above, cyclo(L-phenylalanyl-L-histidine) is activated by freeze drying.

Embodiments 21-103

A vial was charged with 13.5% w/v of racemic alpha-cyano-3-phenoxybenzyl alcohol solution in 0.6M of toluene followed by a 5% w/v excess of (4-chlorophenyl)isopropylketene and 4 m% of a catalyst. The resulting mixture was stirred at 25° C. for a period of time until the reaction had essentially gone to completion or was terminated.

The catalyst used and the predominant isomer are set forth in the Table below in which the symbols used to describe the catalyst are standard in peptide chemistry, e.g. as set forth in Schroder and Lubke, "The Peptide", Vol. II, pages XI–XXVI (1966); and the isomers are A$\alpha$=S-acid S-alcohol isomer, A$\beta$=S-acid R-alcohol isomer, B$\alpha$=R-acid S-alcohol isomer and B$\beta$=R-acid R-alcohol isomer.

TABLE

| Embodiment | Catalyst | Time (hours) | % Predominant Isomer |
|---|---|---|---|
| 21 | cyc(2-pyridylal-L-Phe) | 4 | B$\alpha$ = 29.8 |
| 22 | cyc(D-Phe—L-His) | <28 | B$\beta$ = 38.0 |
| 23 | cyc(L-Trp—L-Trp) | >36 | B$\beta$ = 28.1 |
| 24 | Z—L-Leu—L-His—Me ester | 6.5 | A$\alpha$ = 32.4 |
| 25 | D-Histidine (free base) | >36 | B$\beta$ = 30.0 |
| 26 | D-His—Me ester.2HCl | 30 | A$\alpha$ = 29.3 |
| 27 | L-Phe | >30 | A$\beta$ = 30.0 |
| 28 | Ser—Me ester.HCl | >36 | A$\alpha$, B$\beta$ = 27.0 each |
| 29 | cyc(L-Leu—L-His) | 30 | A$\alpha$ = 29.4 |
| 30 | cyc(Gly—L-Trp) | >36 | B$\beta$ = 36.7 |
| 31 | cyc(D-Phe—D-Trp) | >52 | A$\beta$ = 36.7 |
| 32 | cyc(D-Phe—L-His) | <36 | B$\beta$ = 36.4 |
| 33 | cyc(L-Phe—L-Phe) | >52 | A$\beta$, B$\alpha$ = 27.8 each |
| 34 | cyc(L-Phe—L-Met) | >52 | B$\beta$ = 31.8 |
| 35 | cyc(D-Phe—D-His) | 4 | A$\alpha$ = 40.7 |
| 36 | N—Acetyl—L-His.H$_2$O | 30 | B$\beta$ = 30.6 |
| 37 | Z—D-Phe—L-His Me ester | 28 | B$\beta$ = 28.5 |
| 38 | cyc(L-HomoPhe—L-His) | <18 | A$\alpha$ = 29.9 |
| 39 | cyc(L-Phe—L-3-Me—His) | 1.5 | B$\beta$ = 35.8 |
| 40 | (L-Phe)$^4$.3H$_2$O | >100 | B$\alpha$ = 27.0 |
| 41 | BOC—D-Phe | 6.5 | A$\beta$, B$\alpha$ = 29.9 each |
| 42 | N—Acetyl—L-Trp | 120 | B$\alpha$ = 29.2 |
| 43 | N—Acetyl—L-Trp Et ester | 120 | A$\beta$ = 30.9 |
| 44 | (+)-cis cyclohexane with N(H)—C(O)C$_6$H$_5$ and COOH substituents | 120 | B$\alpha$ = 32.6 |
| 45 | (+)-cis cyclohexane with C(H)—CH$_2$C$_6$H$_5$ and CH$_2$OH substituents | >100 | B$\alpha$ = 28.7 |
| 46 | N—alpha-Acetyl—L-Orn | >120 | B$\alpha$ = 26.3 |
| 47 | L-Phenylalaninol | >120 | A$\alpha$ = 25.5 |
| 48 | L-Carnosine | 80 | A$\alpha$ = 36.8 |
| 49 | L-(−)-Sparteine | 1 | B$\alpha$ = 28.8 |
| 50 | N—Benzyl—im-Benzyl—L-His | 0.5 | B$\beta$ = 33.0 |
| 51 | N—Z—His—p-NO$_2$—L-Phe—L-Phe—OMe | 6.5 | A$\alpha$ = 38.4 |
| 52 | cyc(L-Tyr—L-His) | >6 <24 | B$\beta$ = 32.7 |
| 53 | N—Z—L-His | 30 | A$\alpha$ = 32.4 |
| 54 | Brucine | 0.25 | B$\alpha$ = 32.4 |
| 55 | Nicotine | 1 | A$\beta$ = 28.8 |
| 56 | cyc(N—Ac—L-Phe—N—Ac—Gly) | 74 | B$\alpha$, B$\beta$ = 25.8 each |
| 57 | cyc(L-Val—L-His) | 80 | A$\alpha$ = 38.1 |
| 58 | cyc(L-Phe—Gly) | 5 days | B$\alpha$ = 26.8 |
| 59 | cyc(L-Phe—L-His) | <22 | B$\beta$ = 38.1 |
| 60 | L-Benzyl Hydantoin | >50 <74 | A$\beta$ = 26.9 |
| 61 | alpha-N—Me—L-His | 24 | B$\beta$ = 31.0 |
| 62 | alpha-N—Benzyl—L-His | 6.5 | A$\alpha$, B$\beta$ = 30.6 each |
| 63 | Z—L-His—L-Leu.H$_2$O | >8 <22 | B$\alpha$ = 36.6 |
| 64 | N—Z—L-His—Gly | >100 | A$\alpha$ = 37.4 |
| 65 | Gly—L-His.HCl | 100 | A$\alpha$ = 27.3 |
| 66 | L-beta-Aspartyl—L-His | 100 | B$\beta$ = 31.3 |
| 67 | Z—L-His—L-Phe | >8 <22 | A$\alpha$ = 30.0 |
| 68 | BOC—L-Phe—L-His—OMe | >22 <72 | A$\alpha$ = 27.6 |
| 69 | AOC—L-Phe—L-His—OMe | >8 <22 | A$\alpha$ = 29.5 |
| 70 | BOC—D-PhGly—D-His—OMe | 4 | B$\beta$ = 34.2 |

TABLE-continued

| Embodiment | Catalyst | Time (hours) | % Predominant Isomer |
|---|---|---|---|
| 71 | t-BOC—N$^{im}$—benzyl—L-His | 1 | Bβ = 31.0 |
| 72 | t-BOC—N$^{im}$im-tosyl-L-His | >54 <72 | Bβ = 27.0 |
| 73 | (structure: imidazole-containing bicyclic diketopiperazine) | 46 | Bβ = 28.4 |
| 74 | L-Histidinol.2HCl | 28 | Aα = 30.5 |
| 75 | L-beta-Imidazole Lactic acid | 22-100 | Bβ = 32.2 |
| 76 | N—Z—L-Trp | >100 | Bα = 28.5 |
| 77 | N—Z—L-Trp—p-NO$_2$Ph ester | >100 | Aβ = 31.8 |
| 78 | Z—D-Phe—D-Trp—OMe | >100 | Bα = 28.5 |
| 79 | alpha-N—Benzoyl—L-Arginine | >100 | Bα = 28.8 |
| 80 | N—alpha-Benzoyl—L-Argininamide.HCl.H$_2$O | >100 | Bα = 28.2 |
| 81 | N—alpha-Acetyl—L-Lysine | >100 | Bα = 29.2 |
| 82 | N—alpha-Acetyl—L-Lysine—OMe.HCl | 100 | Aβ = 28.2 |
| 83 | Cyc(L-Val—Gly) | 100 | Bα = 28.6 |
| 84 | 3-Me—His—OMe.2HCl | >8 <22 | Aα = 31.2 |
| 85 | Cyc(Gly—L-His) | 30 | Bβ = 32.9 |
| 86 | Poly-L-Histidine | <46 | Aβ = 31.4 |
| 87 | Z—L-His—L-Phe—L-Phe.OEt | 6.5 | Bβ = 32.9 |
| 88 | N—alpha-Benzoyl—L-His—OMe.HCl | >10 <22 | Aα = 31.5 |
| 89 | t-BOC—L-His | >30 <46 | Aα = 30.8 |
| 90 | L-pGlu—L-His—Gly—NH$_2$ | 9 | Bβ = 35.6 |
| 91 | L-pGlu—L-His—Gly—HOAc | 0.5 | Aβ = 30.2 |
| 92 | L-beta-Ala—L-3-Me—His.HNO$_3$ | 6 | Aα = 35.3 |
| 93 | N—3,5-DNPyr—L-His | >6 <54 | Aα = 28.8 |
| 94 | l-Ph—CH(OH)—CHN(Me)$_2$ (with CH$_3$) | 3.5 | Bβ = 26.9 |
| 95 | Z—D-Phe—NHCH$_2$-(pyridyl) | 4.5 | Aβ = 29.2 |
| 96 | N—Benzoyl—L-His | <46 | Aα = 30.3 |
| 97 | N—ε-Acetyl—L-Lysine | >72 | Aβ = 31.4 |
| 98 | alpha-N—Benzoyl—L-Arg.OEt.HCl | >46 <54 | Aβ = 26.9 |
| 99 | Z—D-Phe—NH-(pyridyl) | 3.5 | Bα = 26.5 |
| 100 | L-p-Glu—L-His—L-Pro.NH$_2$ | 6 | Bβ = 35.3 |
| 101 | Cyc(L-+-Phegly—L-His) | 24 | Aα = 32.4 |
| 102 | Cyc(1-Me—L-His—L-Phe) | 10 min | Bβ = 41.3 |
| 103 | Cyc(2-naphthylala—L-His) | >6 <24 | Bβ = 34.6 |
| 104 | Z—L-Phegly—L-His—OMe | 7 | Aα = 32.8 |
| 105 | Z—L-Homophe—L-His—OMe | <23 | Bβ = 30.6 |
| 106 | cyc(D-Phe—D-His)—C(O)—t-C$_4$H$_9$ | >7, <22 | Aα = 38.9 |
| 107 | Angiotensin II Pentapeptide (Tyr—Ile—His—Pro—Phe) | 48 | Aα = 34.4 |
| 108 | Z—Renin Substrate (Z—Pro—Phe—His—Leu—Leu—Val—Tyr—Ser—beta-naphthylamide) | >24, <48 | Aα = 42.1 |
| 109 | Glucagon-Hexapeptide (L-His—L-Ser—L-Glu—Gly—L-Thr—L-Phe) | >24, <48 | Aα = 31.1 |

What is claimed is:

1. A catalyst which comprises a cyclo(D-phenylalanyl-D-histidine) dipeptide.
2. Cyclo(D-phenylalanyl-D-histidine).

* * * * *